… … …

United States Patent [19]

Ishida et al.

[11] Patent Number: 5,186,852
[45] Date of Patent: Feb. 16, 1993

[54] P,P'-DINONYLDIPHENYLAMINE AND COMPOSITION CONTAINING THE SAME

[75] Inventors: Noboru Ishida, Kawasaki; Hiroyuki Takashima, Yokohama, both of Japan

[73] Assignee: Nippon Oil Co., Ltd., Tokyo, Japan

[21] Appl. No.: 462,013

[22] Filed: Jan. 8, 1990

[30] Foreign Application Priority Data

Jan. 13, 1989 [JP] Japan .................. 1-4693

[51] Int. Cl.⁵ .......................... C10M 133/04
[52] U.S. Cl. ....................... 252/50; 252/401; 564/433
[58] Field of Search ............... 564/433; 252/401, 50

[56] References Cited

U.S. PATENT DOCUMENTS

| | | | |
|---|---|---|---|
| 2,943,112 | 6/1960 | Popoff et al. | 564/409 |
| 3,505,225 | 4/1970 | Wheeler | 252/47.5 |
| 3,944,492 | 3/1976 | Wheeler | 252/50 |
| 4,064,039 | 12/1977 | Nebzydoski et al. | 252/50 |
| 4,767,553 | 8/1988 | Hart et al. | 252/47.5 |
| 4,770,802 | 9/1988 | Ishida et al. | 252/50 |
| 4,897,210 | 1/1990 | Newsoroff | 252/41 |

FOREIGN PATENT DOCUMENTS 181396 8/1987 Japan .

OTHER PUBLICATIONS

Ishida et al., *Chemical Abstracts* 108:24440t (1988).
Ishida et al., *Chemical Abstracts* 108:8679x (1988).

*Primary Examiner*—Richard L. Raymond
*Assistant Examiner*—Scott C. Rand
*Attorney, Agent, or Firm*—Bucknam and Archer

[57] ABSTRACT

A composition prepared by adding a p,p'-dinonyldiphenylamine represented by the following general formula:

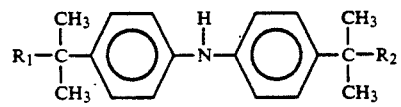

wherein $R_1$ and $R_2$ may be the same or different from each other and each stand for a branched alkyl group having 6 carbon atoms,
and an N-p-alkylphenyl-α-naphthylamine represented by the following general formula:

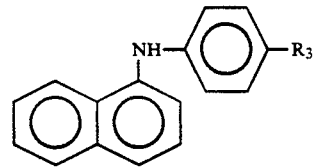

wherein $R_3$ is an alkyl group having 12 to 15 carbon atoms derived from a propylene oligomer,
as essential components to a mineral oil having an aromatic content of 30% by weight or below and/or a synthetic oil containing no aromatic ring in its structural unit.

5 Claims, 4 Drawing Sheets

P,P'-DINONYLDIPHENYLAMINE AND COMPOSITION CONTAINING THE SAME

BACKGROUND OF THE INVENTION

1. Field of the Invention

The present invention relates to a novel branched alkyl-substituted diphenylamine and a composition containing said amine. Particularly, it relates to a novel branched alkyl-substituted diphenylamine excellent in oxidation-inhibiting property and a composition excellent in oxidation resistance containing said amine.

2. Prior Art

A mineral oil having a low aromatic content or a synthetic oil containing no aromatic ring in its structural unit, such as poly-α-olefin oil, is available as a product having high oxidation resistance by virtue of its high responsiveness to an antioxidant, though such a mineral or synthetic oil is poor in oxidation resistance in itself. However, such an oil has disadvantage of poor solvency for an antioxidant. Meanwhile, an antioxidant itself undergoes conversion when it fulfills its function and the conversion product resulting from oxidation is problematic if it forms sludge.

Japanese Patent Appln. Laid-Open Gazette No. (Sho.) 59-5146 discloses that some p,p'-dialkyldiphenylamines are useful as additives for lubricants, elastomers and so on and that the amines exhibit oxidation-inhibiting effects. However, the amines are disadvantageous in that the conversion products thereof are poor in oil solubility to form sludges.

SUMMARY OF THE INVENTION

An object of the present invention is to provide a novel alkyl-substituted diphenylamine excellent in oxidation-inhibiting performance and a composition containing said amine.

The inventors of the present invention have made studies with their attentions paid to the high oxidation-inhibiting performance of a diphenylamine to overcome its disadvantage of forming a sludge and have found that when a diphenylamine having a specific structure is added to oil or the like, it exhibits excellent oxidation-inhibiting performance with less sludge. The present invention has been accomplished on the basis of this finding.

Namely, the present invention provides a p,p'-dinonyldiphenylamine represented by the following general formula:

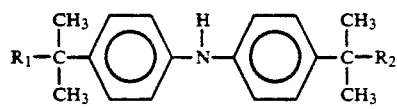

wherein $R_1$ and $R_2$ may be the same or different from each other and each stand for a branched alkyl group having 6 carbon atoms.

Further, the present invention provides a composition prepared by adding a p,p'-dinonyldiphenylamine represented by the following general formula:

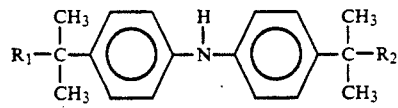

wherein $R_1$ and $R_2$ may be the same or different from each other and each stand for a branched alkyl group having 6 carbon atoms, as an essential component to a mineral oil having an aromatic content of 30% by weight or below and/or a synthetic oil containing no aromatic ring in its structural unit.

Furthermore, the present invention provides a composition prepared by adding a p,p'-dinonyldiphenylamine represented by the following general formula:

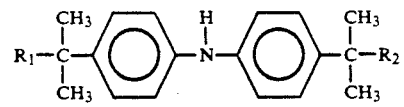

wherein $R_1$ and $R_2$ may be the same or different from each other and each stand for a branched alkyl group having 6 carbon atoms, and an N-p-alkylphenyl-α-naphthylamine represented by the following general formula:

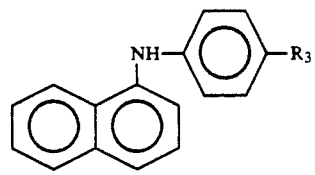

wherein $R_3$ is an alkyl group having 12 to 15 carbon atoms derived from a propylene oligomer, as essential components to a mineral oil having an aromatic content of 30% by weight or below and/or a synthetic oil containing no aromatic ring in its structural unit.

BRIEF DESCRIPTION OF THE INVENTION

The present invention will now be described in more detail.

The p,p'-dinonyldiphenylamine of the present invention is a compound represented by the following general formula:

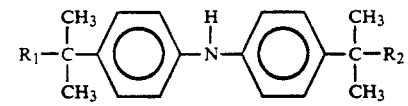

In the above formula, $R_1$ and $R_2$ may be the same or different from each other and each stand for an alkyl group having 6 carbon atoms.

According to the present invention, the above

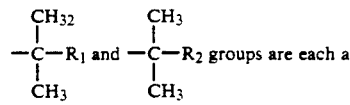

groups are each a branched alkyl group derived from a branched nonene, particularly preferably one derived from a propylene trimer.

A compound represented by the above general formula wherein $R_1$ and $R_2$ are straight-chain alkyl groups even when they have each 6 carbon atoms is unfavorable, because such a compound is liable to settle as a sludge in oil when oxidized.

Further, a compound represented by the above general formula wherein $R_1$ and $R_2$ have less than 6 carbon atoms even when the groups represented by

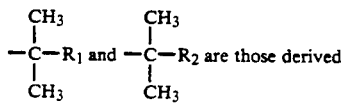

from a propylene oligomer is unfavorable, because such a compound is also liable to settle as a sludge in oil when oxidized. Furthermore, a compound as described above wherein $R_1$ and $R_2$ have more than 6 carbon atoms is also unfavorable, because the proportion of the functional group in the molecule is too low to exhibit a sufficiently high oxidation-inhibiting power.

Particular examples of the groups $R_1$ and $R_2$ of the p,p'-dinonyldiphenylamine of the present invention include

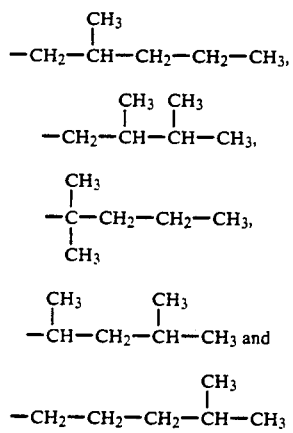

Although the process for the preparation of the p,p'-dinonyldiphenylamine of the present invention may be any arbitrary one, that is, the amine of the present invention can be prepared by any known process, the Friedel-Crafts alkylation process using diphenylamine and propylene trimer is preferable from the standpoint of the easiness of synthesis.

Examples of the catalyst to be used in the process include metal halides such as aluminum chloride, zinc chloride and iron chloride and acid catalysts such as sulfuric and phosphoric acids, phosphorus pentaoxide, boron fluoride, acid clay and activated clay, among which activated clay is particularly advantageous in that the product is not discolored, that the conversion is high and that the removal of the catalyst is easy. Further, the use of a mixed catalyst system comprising activated clay and aluminum chloride at a weight ratio of the former to the latter of from 3 to 10 brings about a further enhanced conversion. The Friedel-Crafts alkylation is generally carried out according to the procedure which will now be described.

That is, 1 mol of diphenylamine, 2 to 20 mol, preferably 3 to 10 mol of a propylene trimer and 50 to 300g, preferably 100 to 200g of activated clay are placed in a reaction vessel fitted with a temperature sensor, a nitrogen-gas inlet tube, a reflux condenser and a stirrer and heated to 135° to 142° C. under stirring. When aluminum chloride is simultaneously used as a catalyst, one-third to one-tenth as much aluminum chloride as the clay used is further added in portions thereafter. Then, the reaction is continued at that temperature while sampling the reaction mixture at regular intervals and analyzing the sampled mixture by gas chromatography or infrared spectroscopic analysis. The heating and the stirring are continued until the content of unreacted diphenylamine is lowered to 10% or below as determined thereby. After the completion of the reaction, the reaction mixture is cooled and filtered with suction to remove the catalyst. The filtrate is distilled under a reduced pressure to remove unreacted propylene trimer. The residue is purified by chromatography to obtain the objective p,p'-dinonyldiphenylamine as a viscous transparent liquid.

When the p,p'-dinonyldiphenylamine of the present invention is added to a base oil such as mineral or synthetic oil, it serves as an antioxidant for the base oil.

The base oil to be used in the present invention must be mineral oil having an aromatic content of 30% by weight or below and/or a synthetic oil containing no aromatic ring in its structural unit.

The mineral oil is generally one having a kinematic viscosity at 40° C. of 10 to 10,000 cSt, preferably 20 to 1,000 cSt. It is generally preferable to use a mineral oil prepared by distilling a crude oil to recover a lubricant fraction and purifying the lubricant fraction by arbitrary means such as solvent refining, sulfuric acid treatment, hydrogenation or clay filtration.

It is suitable that the mineral oil have an aromatic content of 30% by weight or below, preferably 20% by weight or below. The term "aromatic content" as used in this specification refers to a value as determined according to ASTM D2549-81.

On the other hand, the synthetic oil to be used in the present invention must not contain any aromatic ring in its structural unit and generally has kinematic viscosity at 40° C. of 10 to 10,000 cSt. Particular examples thereof include poly-α-olefin oils prepared by the (co)polymerization of a $C_{4\sim 30}$ α-olefin, such as polybutene and decene-1 oligomer; monoesters of aliphatic monocarboxylic acid with aliphatic monohydric alcohol, represented by butyl stearate and methyl laurate; diesters of aliphatic dibasic acid with aliphatic monohydric alcohol, represented by di-2-ethylhexyl sebacate, dioctyl adipate and ditridecyl glutarate; esters of aliphatic polyhydric alcohol with aliphatic monocarboxylic acid, represented by trimethylolpropane caprylate, trimethylolpropane pelargonate, pentaerythritol 2-ethylhexanoate and pentaerythritol pelargonate; polyalkylene glycols and monoalkyl ethers, dialkyl ethers, monoalkyl esters and dialkyl esters thereof, represented by polyethylene glycol and polypropylene glycol; cycloparaffins such as cyclodonecane, hydrindan, dicyclohexyl and tercyclohexyl; alkyl-cycloparaffins such as dicyclohexylbutane and dicyclohexylpropane and mixtures thereof.

The amount of the p,p'-dinonyldiphenylamine of the present invention to be added to a base oil as described above to prepare a composition is preferably 0.01 to 10% by weight, still preferably 0.1 to 5.0% by weight based on the composition.

Although a composition prepared by adding the p,p'-dinonyldiphenylamine of the present invention to the base oil is as such excellent in oxidation resistance and hardly forms sludge, the excellent performance of the composition can be further improved by the additional use of an N-p-alkylphenyl-α-naphthylamine represented by the following general formula:

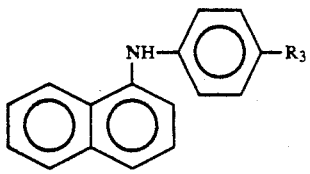

wherein $R_3$ is a branched alkyl group having 12 to 15 carbon atoms derived from a propylene oligomer.

The group $R_3$ of the N-p-alkylphenyl-α-naphthylamine must be a branched alkyl group derived from a propylene oligomer. If the group $R_3$ is a branched alkyl group derived from an α-olefin, the resulting compound will have much inferior oxidation-inhibiting performance to that of the N-p-alkylphenyl-α-naphthylamine according to the present invention. Further, if the group $R_3$ is a group derived from an oligomer of an olefin other than propylene, such as isobutylene, the resulting compound will unfavorably be oxidized in itself to settle as a sludge in oil.

If the group $R_3$ has a number of carbon atoms lower than the lower limit according to the present invention, the resulting compound will be liable to settle as a sludge in oil after it has fulfilled the antioxidant action, even if the group $R_3$ is a branched alkyl group derived from a propylene oligomer. On the contrary, if the group $R_3$ has a number of carbon atoms exceeding the upper limit according to the present invention, the proportion of the functional group in the molecule will unfavorably be low to result in a lowered oxidation-inhibiting power.

The process for the preparation of the N-p-alkylphenyl-α-naphthylamine is disclosed in detail in Japanese Patent Appln. Laid-Open Gazette No. (Sho.) 62-181396 which has been filed by the applicant of the present invention.

The amount of the above N-p-alkylphenyl-α-naphthylamine to be added to a composition comprising the base oil and the p,p'-dinonyldiphenylamine is preferably 0.01 to 10% by weight, still preferably 0.1 to 5.0% by weight, based on the total amount of the composition.

If necessary, the composition of the present invention may further contain conventional additives and examples thereof include antioxidant, detergent-dispersant, viscosity index improver, pour point depressant, oiliness improver, wear resistance improver, extreme pressure agent, corrosion inhibitor, metal deactivator, rust preventive, defoaming agent, emulsifier, demulsifier, bacterioxide and coloring agent. These additives are described in more detail in, for example, "Junkatsu-yu Gakkai Shi Vol. 15 No. 6" or Toshio Sakurai "Sekiyu-Seihin Tenkazai (Additives for Petroleum Products)" (Saiwai Shobo). The total amount of the additives to be added is at most 10% by weight, preferably at most 5% by weight, still preferably at most 3% by weight, based on the total amount of the lubricant.

The composition of the present invention is useful as various lubricants and examples thereof include gasoline engine oil, diesel engine oils such as land diesel engine oil and marine diesel engine oil; turbine oils such as additive-free turbine oil, additive-containing turbine oil, gas turbine oil and marine turbine oil; gear oils such as automotive gear oil, industrial gear oil and automatic transmission oil; metal working oils such as hydraulic fluid, compressor oil, refrigerator oil, cutting oil, grinding oil, plastic working oil, heat treatment oil and electrospark machining oil; sliding guide way oil and bearing oil. Further, the composition can be also favorably used as insulation oil such as transformer oil, breaker oil, cable oil or capacitor oil, anti-corrosive oil, heat transfer oil, grease or vacuum pump oil.

EMBODIMENT

The present invention will now be described in more detail by referring to the following Examples and Comparative Examples.

EXAMPLE 1

169 g (1 mol) of diphenylamine, 1009 g (8 mol) of a propylene trimer and 150 g of activated clay having a specific surface area of 235 m$^2$/g and an acidity of 1.5 mgKOH/g were placed in a four-necked flask, followed by stirring. The contents were heated in a stream of nitrogen to carry out a reaction at the boiling point of the propylene trimer for 10 hours. After the completion of the reaction, the activated clay was filtered out and the filtrate was distilled under a reduced pressure to remove unreacted propylene trimer. The residue was purified by chromatography to obtain 365g of the objective p,p'-dinonyldiphenylamine having a structure represented by the formula which will be described below, as an isomer mixture of pale yellow, transparent and viscous liquid.

The elemental analysis of the obtained compound revealed that the compound comprised 85.6% by weight of carbon, 11.4% by weight of hydrogen and 3.2% by weight of nitrogen. The yield based on diphenylamine was 86%.

Figure 1:
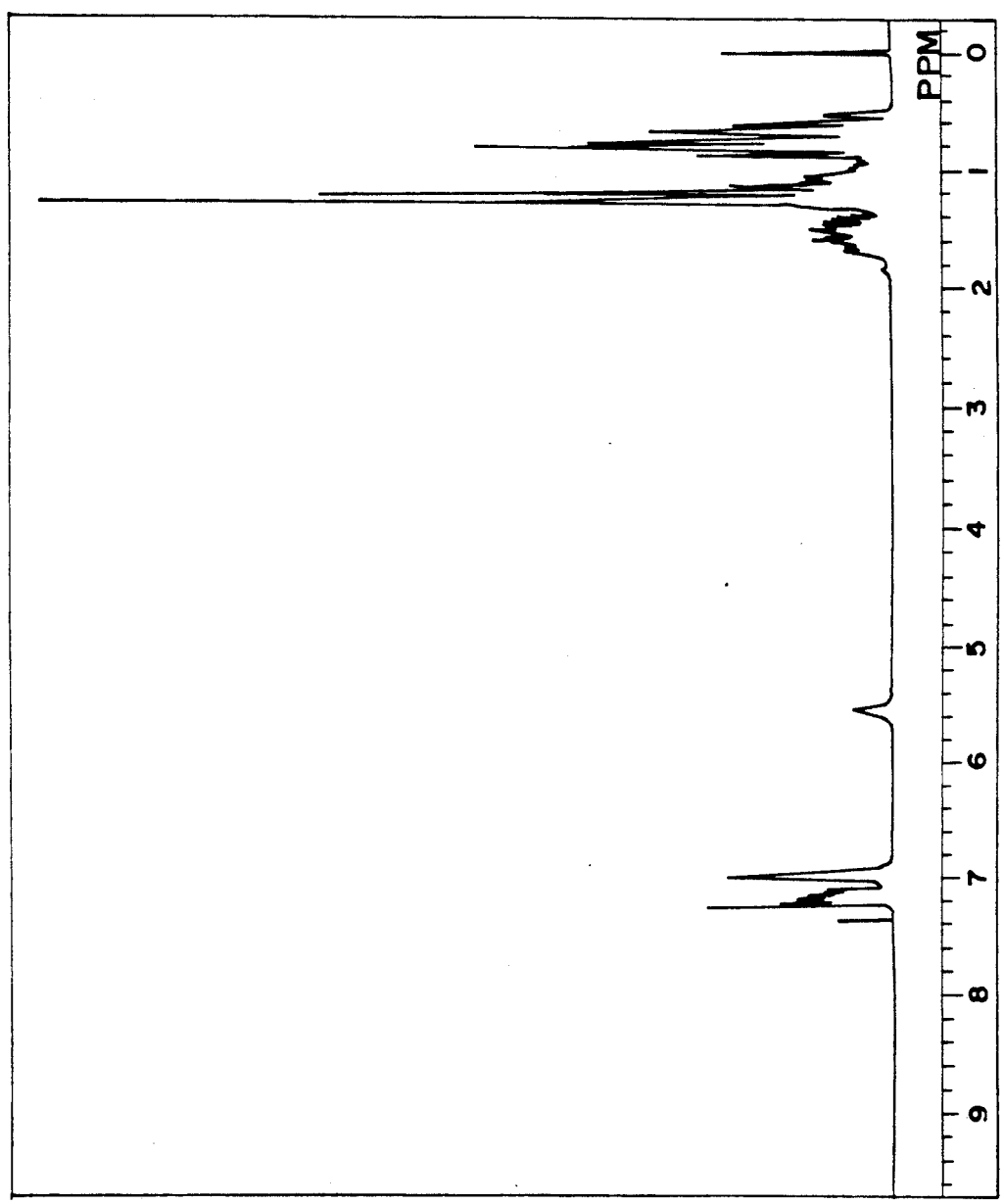
FIG. 1 is a chart showing the $^1$H NMR spectrum of the p,p'-dinonyldiphenylamine.
Figure 2:
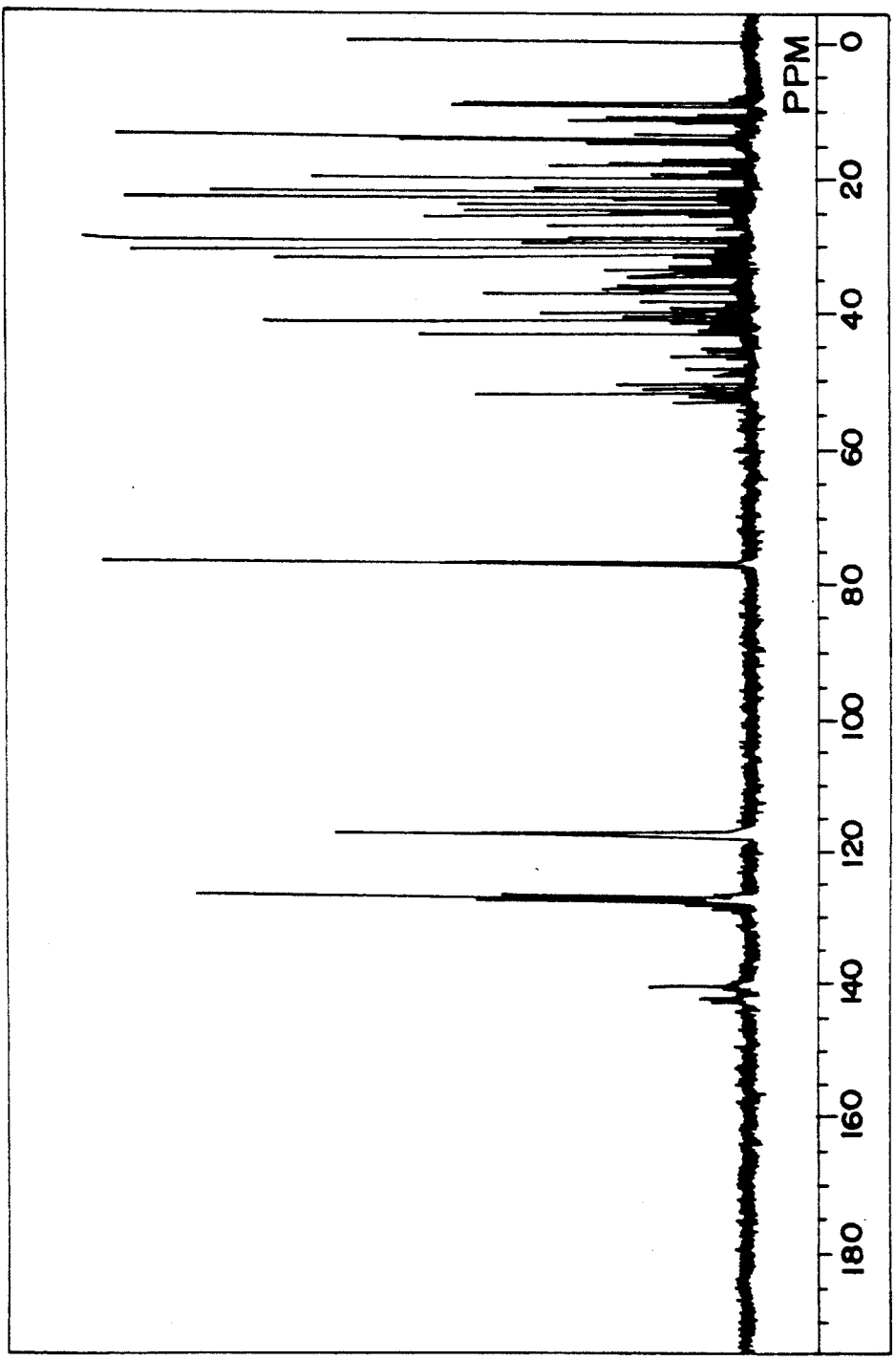
FIG. 2 is a chart showing the $^{13}$C NMR spectrum of the compound.
Figure 3:
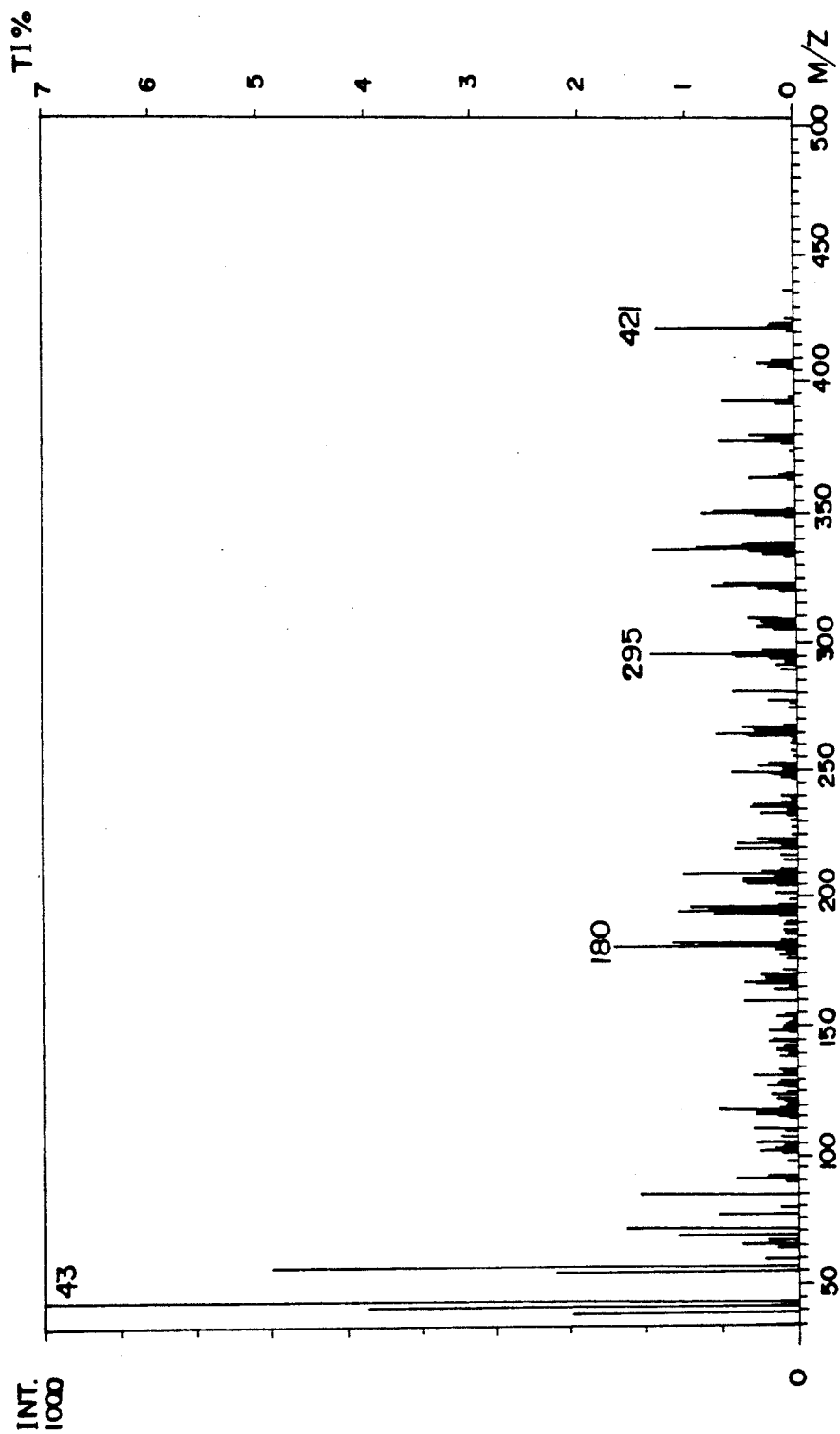
FIG. 3 is a chart showing the mass spectrum of the compound.
Figure 4:
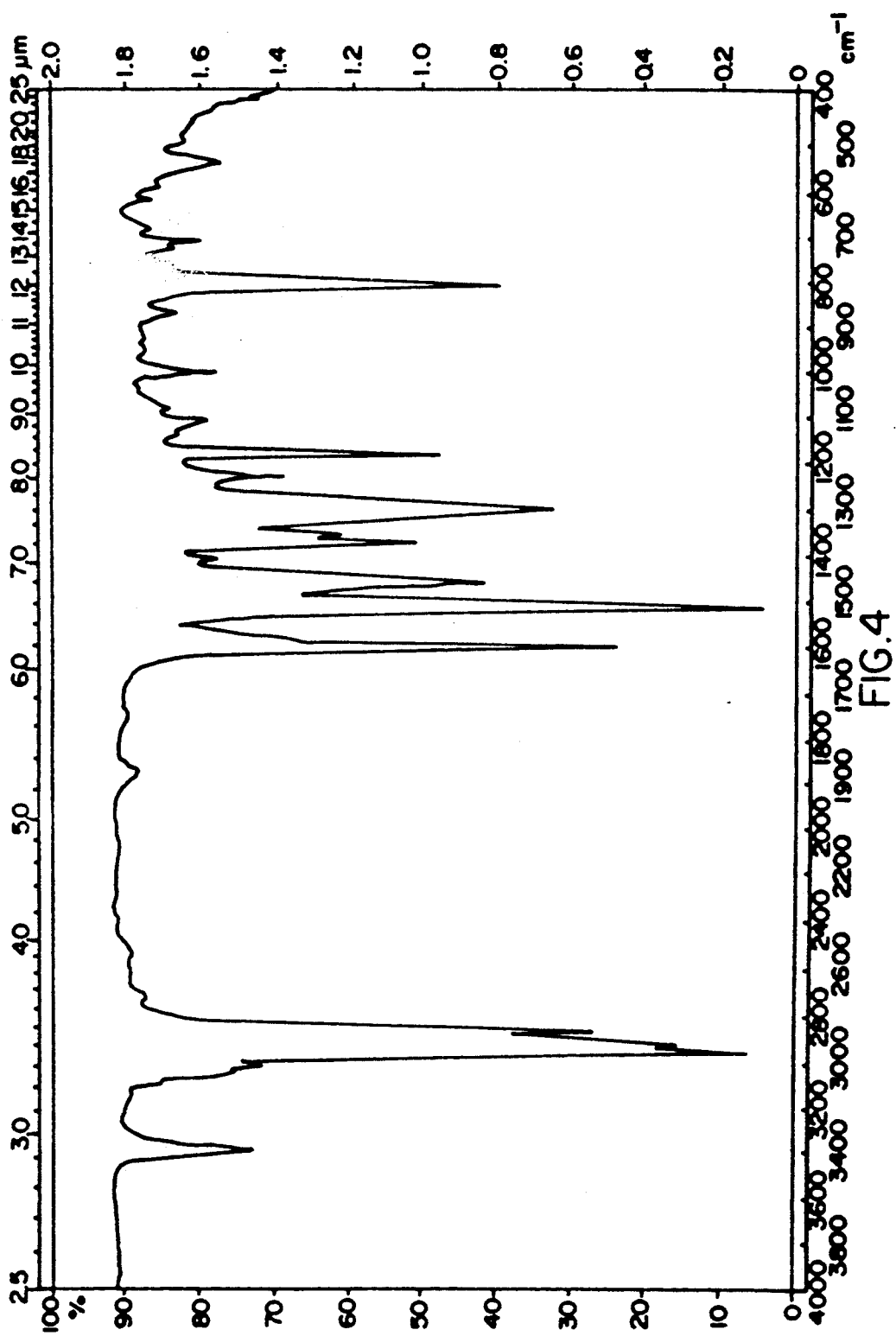
FIG. 4 is a chart showing the IR spectrum of the compound.

The $^1$H NMR spectrum, $^{13}$C NMR spectrum, mass spectrum and IR spectrum of the compound are shown in FIGS. 1 to 4, respectively.

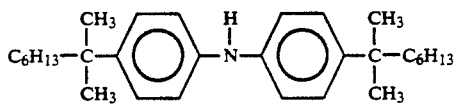

EXAMPLE 2 AND COMPARATIVE EXAMPLE 1

The conversion product resulting from the oxidation (i.e., after functioning as the antioxidant) of the p,p'-dinonyldiphenylamine prepared in Example 1 was added in an amount specified in Table 1 to a purified mineral oil having an aromatic content of 7% by weight (kinematic viscosity: 34.4 cSt at 40° C.) and a poly-α-olefin oil (decene-1 oligomer, kinematic viscosity: 30.7 cSt at 40° C.) respectively to determine the solubilities of the conversion product in these oils (Example 2). The results are shown in Table 1.

For comparison, as shown in Table 1, a commercially available p,p'-dioctyldiphenylamine antioxidant having alkyl substituents derived from an isobutylene dimer was examined for the solubility of the conversion product thereof in a base oil in a similar manner to that described above (Comparative Example 1). The results are also shown in Table 1.

The conversion products resulting from the oxidation of the p,p'-dinonyldiphenylamine and the p,p'-dioctyldiphenylamine were prepared by the method of R. F. Bridger (see J. Org. Chem., Vol. 33, No. 12 (1968)) according to the procedure which will now be described.

That is, 0.05 mol of p,p'-dinonyldiphenylamine or p,p'-dioctyldiphenylamine was dissolved in 100 ml of acetone and the obtained solution was cooled to 0° C. After 2.63 g of potassium permanganate was added to the solution in portions over a period of 5 hours, the cooling was stopped. The obtained mixture was allowed to stand at a room temperature for 15 hours, while keeping the system in nitrogen atmosphere. The reaction mixture was passed through a filter paper to remove manganese dioxide and the filtrate was distilled to remove the acetone. The residue was dissolved in 100 ml of benzene and the obtained solution was washed with water and distilled to remove the benzene.

The product thus prepared was ascertained by IR absorption spectrum, GPC analysis and mass spectrometric analysis to comprise the conversion product resulting from the oxidation of p,p'-dinonyldiphenylamine or p,p'-dioctyldiphenylamine as a main component.

EXAMPLE 3 AND COMPARATIVE EXAMPLE 2

In a similar manner to that of Example 2, the conversion product of the p,p-dinonyldiphenylamine prepared in Example 1 and that of N-p-dodecylphenyl-α-naphthylamine (the branched alkyl group was one derived from a propylene tetramer) were simultaneously added to the same purified mineral oil and poly-α-olefin oil as those used in Example 2 respectively to determined the solubility of the conversion products (Example 3).

For comparison, in a similar manner to that described above, the conversion product of p,p'-dioctyldiphenylamine and that of N-p-octylphenyl-α-naphthylamine were simultaneously added to the same base oil as that used above to determine the solubility of the conversion products in the base oil (Comparative Example 2). The results are shown in Table 1.

EXAMPLE 4, COMPARATIVE EXAMPLE 3 AND REFERENCE EXAMPLE 1

In order to determine the oxidation-inhibiting performance of the p,p'-dinonyldiphenylamine prepared in Example 1, the p,p'-dinonyldiphenylamine was added, in an a mount specified in Table 2, to the same purified mineral oil and poly-α-olefin oil as those used in Example 2, respectively. The lubricant compositions thus prepared were each subjected to the rotary pump oxidation test according to ASTM D 2272 (test temperature: 150° C., oxygen pressure: 6.3 kg/cm$^2$, room temperature, copper wire catalyst, 10 ml of water). The oxidation-inhibiting performance was evaluated by the time taken until the internal pressure of the vessel was reduced by 1.8 kg/cm$^2$ (Example 4). The results are shown in Table 2.

For comparison, the same p,p'-dioctyldiphenylamine as that used in the foregoing Comparative Example 1 and N-p-branched dodecylphenyl-α-naphthylamine were examined for oxidation-inhibiting performance in a similar manner to that described above (Comparative Example 3 and Reference Example 1). The results are also shown in Table 2. As can be understood from the results of Comparative Example 1 shown in Table 1, in Comparative Example 3, the compound listed in Table 2 was added in such a large amount that the conversing product thereof separated out, i.e., that the resulting composition was in danger of forming sludge to thereby cause a problem in practical use.

EXAMPLE 5 AND COMPARATIVE EXAMPLE 4

In order to determine the oxidation-inhibiting performance exhibited when the p,p'-dinonyldiphenylamine prepared in Example 1 and the N-p-dodecylphenyl-α-naphthylamine according to the present invention are simultaneously used, the compounds were added to the same purified mineral oil as that used in Example 2 in amounts specified in Table 2 to obtain a composition. This composition was subjected to the same test as that made in Example 4 to determine the oxidation-inhibiting performance of this antioxidant system (Example 5).

For comparison, the same antioxidant system of p,p'-dioctylphenylamine and N-p-octylphenyl-α-naphthylamine as that used in Comparative Example 2 was also examined for oxidation-inhibiting performance in a similar manner to that described above (Comparative Example 4). The results of both the examinations are shown in Table 2.

As can be understood from the results of Comparative Example 2 shown in Table 1, in Comparative Example 4, the compounds listed in Table 2 were added in such large amounts that the conversion products thereof separated out, i.e., that the resulting composition was in danger of forming sludge to thereby cause a problem in practical use.

TABLE 1

| Ex. or Comp. Ex. No. | Compound added | Purified mineral oil*1 amount (% by wt.) | solubility | Poly-α-olefin oil*2 amount (% by wt.) | solubility |
| --- | --- | --- | --- | --- | --- |
| Ex. 2 | conversion product of p,p'-branched dinonyldiphenylamine | 3.0 | soluble | 3.0 | soluble |
| Comp. Ex. 1 | conversion product of p,p'-branched dioctyldiphenylamine | 0.5 | soluble | 0.5 | soluble |
|  |  | 1.0 | partially insoluble | 1.0 | partially insoluble |
| Ex. 3 | conversion product of p,p'-branched dinonyldiphenylamine | 3.0 | soluble | 3.0 | soluble |
|  | conversion product of N-p-branched dodecylphenyl-α-naphthylamine | 3.0 |  | 3.0 |  |
| Comp. Ex. 2 | conversion product of p,p'-branched dioctyldiphenylamine | 1.0 | partially | 1.0 | partially |

TABLE 1-continued

| Ex. or Comp. Ex. No. | Compound added | Purified mineral oil[*1] amount (% by wt.) | solubility | Poly-α-olefin oil[*2] amount (% by wt.) | solubility |
|---|---|---|---|---|---|
| | conversion product of N-p-branched octylphenyl-α-naphthylamine[*3] | 1.0 | insoluble | 1.0 | insoluble |

[*1] purified mineral oil having an aromatic content of 7% by weight (kinematic viscosity: 34.4 cSt at 40° C.)
[*2] decene-1-oligomer (kinematic viscosity: 30.7 cSt at 40° C.)

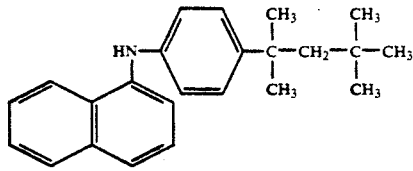

TABLE 2

| Ex., Comp. Ex. or Ref. Ex. No. | Compound added | Purified mineral oil[*1] amount (% by wt.) | oxidation-inhibiting performance (min) | Poly-α-olefin oil[*2] amount (% by wt.) | oxidation-inhibiting performance (min) |
|---|---|---|---|---|---|
| Ex. 4 | p,p'-branched dinonyldiphenylamine | 1.0 | 468 | 1.0 | 1719 |
| | | 2.0 | 480 | | |
| Comp. Ex. 3 | p,p'-branched dioctyldiphenylamine | 1.0 | 435 | 1.0 | 1476 |
| | | 2.0 | 462 | | |
| Ref. Ex. 1 | N-p-branched dodecylphenyl-α-naphthylamine | 2.0 | 1820 | — | — |
| Ex. 5 | p,p'-branched dinonyldiphenylamine | 1.0 | | | |
| | N-p-branched dodecylphenyl-α-naphthylamine | 1.0 | 2154 | — | — |
| Comp. Ex. 4 | p,p'-branched dioctyldiphenylamine | 1.0 | | | |
| | N-p-branched octylphenyl-α-naphthylamine | 1.0 | 2127 | — | — |

It can be understood from the results shown in Table 1 that when the p,p'-dinonyldiphenylamine of the present invention is added alone (Example 2) or together with the N-p-alkylphenyl-α-naphthylamine according to the present invention (Example 3) to the base oil, the conversion product hardly forms sludge in the base oil, so that these antioxidant systems can be added to the base oil in an enhanced amount. On the other hand, p,p'-dioctyldiphenylamine (Comparative Example 1) and a combination thereof with N-p-octylphenyl-α-naphthylamine (Comparative Example 2) are much inferior to the antioxidant systems of Examples 2 and 3 in the solubility of the conversion product thereof. Therefor, the use thereof as an antioxidant is in danger of forming sludge, so that the addition thereof in a large amount is impossible.

Further, it can be understood from the results shown in Table 2 that the compositions of Examples 4 and 5 are out of danger of forming sludge by virtue of the high solubilities of the p,p'-dinonyldiphenylamine, the N-p-alkylphenyl-α-naphthylamine and the conversion products thereof, so that the amounts of the antioxidant systems added can be arbitrarily controlled. Therefor, when high oxidation resistance is required, this requirement can be satisfied by increasing the amount of the antioxidant system.

On the other hand, the antioxidant system of Comparative Example 3 or 4 cannot give any lubricant composition having high oxidation resistance equivalent to that of the composition of the present invention, because the amount of the system added is significantly limited owing to its tendency of forming sludge, as can be though the system is nearly equivalent to the one of the present invention in respect of oxidation-inhibiting performance. Further, the compositions of Comparative Example 3 and 4 each contain such a large amount of the antioxidant system that it is in danger of forming sludge, so that even the oxidation resistance shown in Table 2 cannot be attained in practice.

As described above, a specific mineral or synthetic oil is improved in oxidation resistance by the addition of the p,p'-dinonyldiphenylamine of the present invention alone or together with the N-p-alkylphenyl-α-naphthylamine, with less danger of forming sludge.

What is claimed is:

1. A composition prepared by adding p,p'-dinonyldiphenylamine represented by the following general formula:

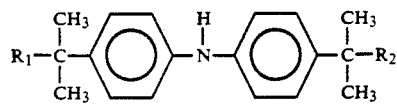

wherein $R_1$ and $R_2$ may be the same or different from each other and each stand for a branched alkyl group having 6 carbon atoms, and an N-p-alkylphenyl-α-naphthylamine represented by the following general formula:

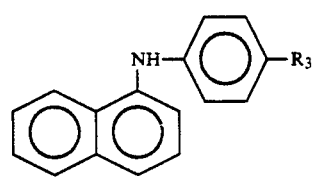

wherein $R_3$ is an alkyl group having 12 to 15 carbon atoms derived from a propylene oligomer, an essential components to a mineral oil having an aromatic content of 30% by weight or below and/or a synthetic oil containing no aromatic ring in its structural unit.

2. The composition according to claim 1 wherein said mineral oil has a kinematic viscosity at 40° C. of 10–10,000 cSt and said synthetic oil has a kinematic viscosity at 40° C. of 10–10,000 cSt.

3. The composition according to claim 1 wherein said dinonyldiphenylamine has the formula

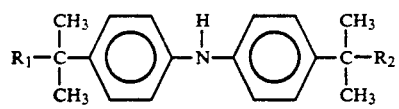

wherein $R_1$ and $R_2$ are the same or different and each is a branched alkyl group having 6 carbon atoms of formula

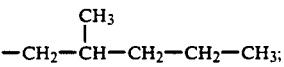

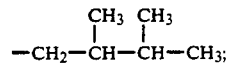

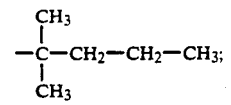

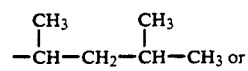

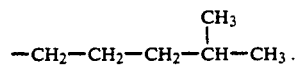

4. The composition according to claim 1 wherein said N-p-alkylphenyl-α-napthylamine is in the amount of 0.01–10% by weight.

5. The composition according to claim 1 wherein said N-p-alkylphenyl-α-naphthylamine is N-p-dodecylphenyl naphthylamine.

* * * * *